United States Patent [19]

Urban et al.

[11] Patent Number: 5,036,708
[45] Date of Patent: Aug. 6, 1991

[54] RHEO-PHOTOACOUSTIC FT-IR SPECTROSCOPIC METHOD AND APPARATUS

[75] Inventors: Marek W. Urban; Hans J. Goettler, both of Fargo, N. Dak.

[73] Assignee: North Dakota State University, Fargo, N. Dak.

[21] Appl. No.: 489,821

[22] Filed: Mar. 9, 1990

[51] Int. Cl.⁵ ............................................. G01N 29/04
[52] U.S. Cl. ...................................... 73/801; 250/305
[58] Field of Search ................... 73/801, 587, 150 A; 364/551.01; 250/305

[56] References Cited
U.S. PATENT DOCUMENTS 4,860,224  8/1989  Cashell et al. ................... 364/551.01

Primary Examiner—Jerry W. Myracle
Attorney, Agent, or Firm—Cushman, Darby & Cushman

[57] ABSTRACT

A rheo-photoacoustic fourier-transform infrared spectroscopic method and apparatus for examining rheological properties of materials on a molecular level. The apparatus comprises an IR spectrometer and a photoacoustic cell for generating frequency-domain photoacoustic information of a specimen under various static load conditions. Relative changes in amplitudes of certain bands in the respective spectra as a function of elongation indicate relative behavior of different molecular bonds in the material thereby to detect individually the behavior or failure mode of the respective molecular bonds. A method of detecting interfacial failure of composite polymeric material includes detecting changes in the profile of the spectrum of the surface layer at successive levels of stretching of the composite material brough about by appearance of spectral responses characteristic of the underlying layer.

25 Claims, 8 Drawing Sheets

RHEO-PHOTOACOUSTIC FT-IR SPECTROSCOPIC METHOD AND APPARATUS

BACKGROUND OF THE INVENTION

This invention pertains to a method and apparatus for examining characteristics of materials on a molecular level using photoacoustic techniques, particularly, the examination of organic polymers.

Photoacoustic analytical techniques discussed herein are drawn from the infrared (IR) spectroscopic and acoustics arts. U.S. Pat. No. 4,255,971 to Rosencwaig, for example, discloses photoacoustic microscopy for examining materials on microscopic level. He also suggests the use of radiant energy, but not for rheo-photoacoustically examining molecular behavior. U.S. Pat. No. 4,875,175 to Egee, et al. also discloses photoacoustic spectroscopic techniques for analyzing thermal properties of layered materials. On the other hand, rheo-photoacoustical properties are measured in accordance with this invention.

It is also known, for instance, that molecular structures of certain chemical compounds produce characteristic energy absorption patterns in the IR spectrum due to their molecular vibration modes of the bonds that join the respective atoms. The molecules generally vibrate in the wave number range of 200 to 4000 cm$^{-1}$. To identify the material, IR spectroscopy alone serves that purpose, if the material is IR transmissive, since each material exhibits a unique frequency IR absorption spectral pattern.

Rheological properties of optically transmissive polymers on a molecular level are described in "Rheo-optical Fourier-transform infrared (FT-IR) spectroscopy of polymers", *Colloid & Polymer Science*, Vol. 262, pp. 223–229, 1984, H. W. Siesler. Siesler, like many other prior infrared spectroscopy techniques, relates molecular events in the material under stress-strain conditions to IR intensities and/or IR band shift measurements.

On a microscopic level, as opposed to molecular level, properties of adhesive bonds or material flaws have also been examined. In the past, stress-wave emission techniques, such as disclosed by U.S. Pat. No. 4,004,456 to Vahaviolos, U.S. Pat. 4,100,808 to Evans et al., U.S. Pat. No. 4,501,149 to Konno, and U.S. Pat. No. 4,538,462 to Hartog were employed. From a rheological standpoint, though, optical systems have been limited to birefringence techniques, such as those described in U.S. Pat. No. 4,840,481 to Spillman, Jr. and U.S. Pat. No. 4,777,358 to Nelson. No rheo-photoacoustical FT-IR techniques relating to vibrational modes of the substance under examination are believed to have been used in the past.

SUMMARY OF THE INVENTION

The present invention provides means for determining the photoacoustic spectra of a test specimen, such as a polymeric material, as a function of IR reabsorption and deformation, despite the specimen's opacity to infrared radiation. To monitor the effect of deformation on the photoacoustic signal, the specimen is subjected to IR irradiation during elongation. IR irradiation produces internal heat and consequent acoustic surface waves. Stressing effects conformational changes and molecular deformation which, in turn, produce additional acoustic waves contributing to the intensity of the photoacoustic spectrum. A sensitive detector senses acoustic energy produced by the specimen during the test. The various frequencies of the sensed acoustic waves, which are Fourier transformed, indicate dynamic events akin to the chemical bonds of the specimen's molecular structure. Likewise, interfacial adhesive properties of polymers can be determined by virtue of observed spectral changes resulting from elongation and shear forces generated in a test specimen.

No prior photoacoustic acoustic systems are known which rheologically examine materials on a molecular level. Furthermore, it is not known in the art to employ FT-IR rheo-photoacoustic techniques to examine the chemical bonds of materials according to their molecular vibrational modes. This invention is thought to present the first such application.

In accordance with the foregoing, the invention comprises a method and apparatus for performing rheological studies on materials. The apparatus comprises IR means for irradiating the specimen with infrared radiation at predetermined frequencies, detecting means for detecting acoustic emissions of said specimen in response to said irradiation, and signal processing means for generating a representation of said molecular characteristic according to a frequency-domain representation of the photoacoustic signal.

A first method comprises the steps of irradiating the material with infrared radiation and detecting photoacoustic acoustic signals generated by the material under differing static or dynamic load conditions. A second method comprises the step detecting an interfacial failure of a composite structure of at least two materials by detecting a change in photoacoustic FT-IR spectrum upon loading.

Other aspects, features and advantages of the invention will become apparent in light of the following description, taken in conjunction with the accompanying drawings. The invention, though, is pointed out with particularity by the appended claim.

DETAILED DESCRIPTION OF THE INVENTION

It is helpful to understand the mechanism by which the material under examination generates photoacoustic signals during rheological examination. In a first stage, the material absorbs IR energy during the irradiation process and produces heat which generates acoustic waves on the surface of the material. In a second stage, a load applied to the material, e.g., elongation, results in conformational changes and deformation in the spatial relationship of the molecules thereof. These changes and deformation release energy due to phase separation, phase changes, crack formation which, in turn, produce additional acoustic surface waves contributing to the overall energy of the acoustic signal. It is found that the majority of the vibrational bands in the acoustic spectrum (corresponding to unique molecular bonds) have different sensitivities to deformation, and change at different rates. Accordingly, one can detect the relative reaction of different chemical bonds during application of loads to the material.

The magnitude of the photoacoustic energy over the IR frequency band is detected and Fourier-transformed to generate representations characteristic of molecular behavior as a function of frequency. Such representations advantageously permit examination of individual chemical bond activity in the molecules of the specimen. Additional background on the theory is described in "A Novel Approach to Photoacoustic FT-IR Spectroscopy: Rheo-Photoacoustic Measurements", *Applied Spectroscopy*, Volume 43, Number 8, 1989, page 1387-1393, by McDonald, et al. which is incorporated herein by reference.

Rheo-photoacoustic FT-IR measurements are useful for determining material strength, deformation, stress-strain, polymer cross-linking, surface interaction of composite structures, diffusion, and other characteristics. Fibers, films, and composite structures may be examined. Rheo-photoacoustic IR measurements of the present invention include spectroscopy of opaque materials which were previously not suitable for examination by I spectroscopy.

Figure 3:
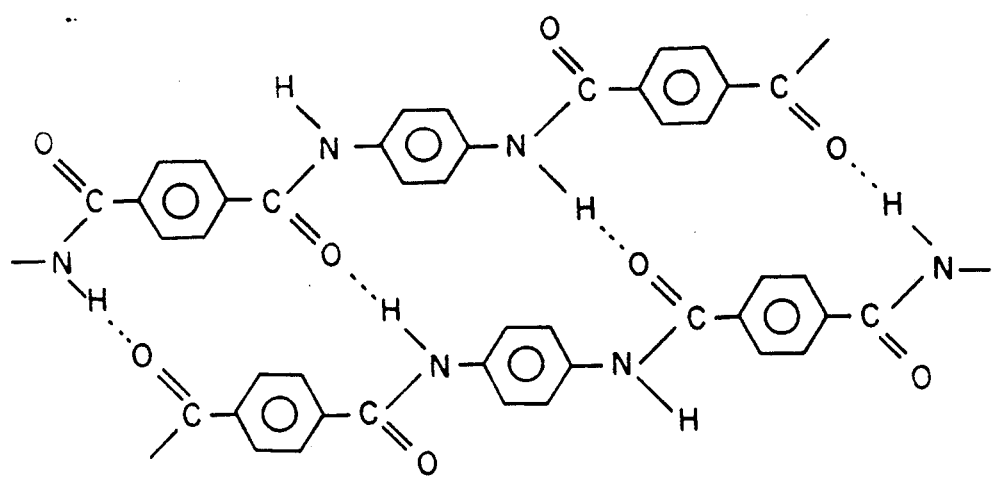
FIG. 3 shows the polymer structure of poly(p-phenylene terephthalamide) useful for explaining the principles of the present invention.

For purposes of illustration herein, the application of rheological photoacoustic measurements is made upon polymers, and in particular, poly(p-phenylene terephthalamide) (PPTA) fibers to determine their molecular behavior during conformational changes and deformation due to elongation and breakage. Also illustrated are measurements of adhesion properties of siloxane-coated polyethylene. Many other materials lend themselves to rheo-photoacoustic FT-IR measurements. For PPTA fibers, the chemical structure of which is depicted in FIG. 3, these measurements indicate points of bond separation under load conditions of nitrogen-hydrogen (N—H), carbon-oxygen (C=O), carbon-carbon (C—C) and carbon-nitrogen (C—N) in PPTA fibers.

Figure 1:
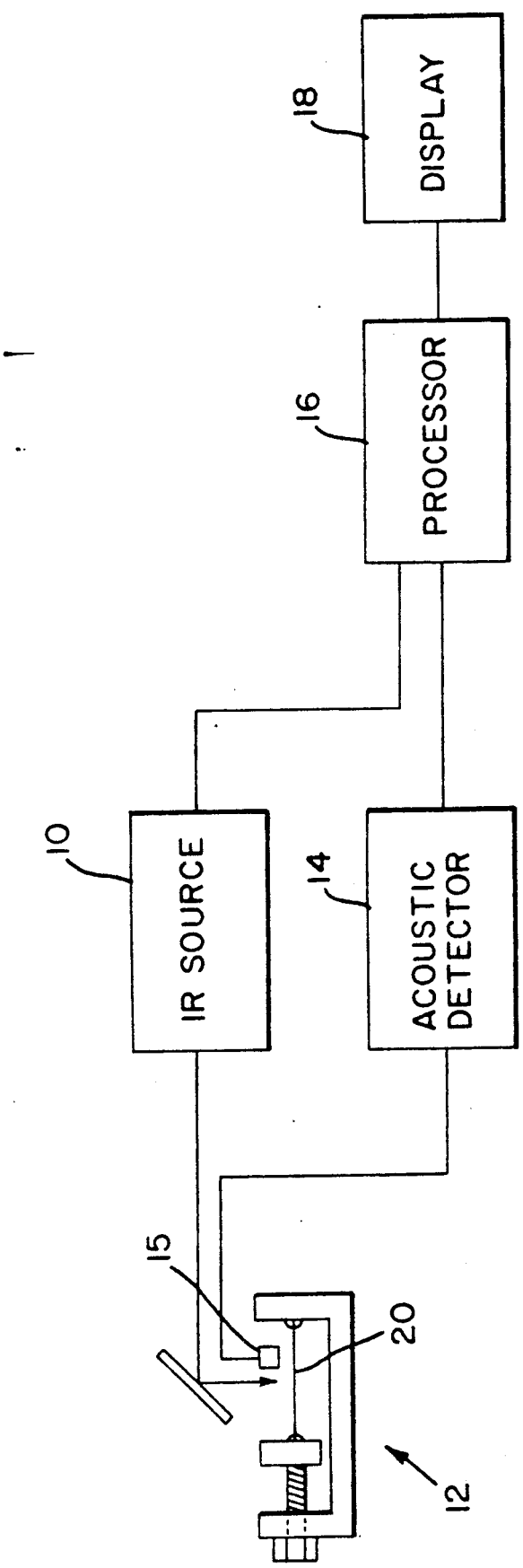
FIG. 1 is a system block diagram of a preferred embodiment of the invention.

FIG. 1 depicts a system diagram and a specimen head of an apparatus for carrying out the principles of the invention. Basic components include an infrared (IR) source 10 for irradiating a specimen 20, a specimen holder generally denoted at 12 for carrying and elongating the specimen 20, a photoacoustic detector 14, a processor 16, and a display 18.

IR source 10 may comprise a Digilab FTS-10M FT-IR spectrometer commercial available from the Digilab division of Bio-Rad Laboratories, Inc. of Cambridge, Massachusetts. An infrared spectrometer is a conventional analytical tool for examining IR absorption spectra of polymeric and other substances. As known, the frequency range of IR spectroscopy corresponds with molecular vibrations of specimens under examination. The photoacoustic detector 14 includes an amplifier and a detector head 15. In actual practice, a sensitive microphone has been found to adequately generate signals of sufficient level when acoustically coupled with the specimen, as subsequently explained in more detail. Processor 16 includes a microprocessor for analyzing acoustic signals generated by the detector 14 in relation to the IR irradiation of the specimen, and for manipulating the spectral data for presentation on display device 18. Display 18 preferably generates graphic depictions of spectral data indicative of molecular characteristics. In a working embodiment, Spectra Calc software in an IBM AT microcomputer was employed to produce spectral information describing the specimen's properties. The specimen holder 12 further includes means for applying a load upon the specimen 20.

Figure 2:
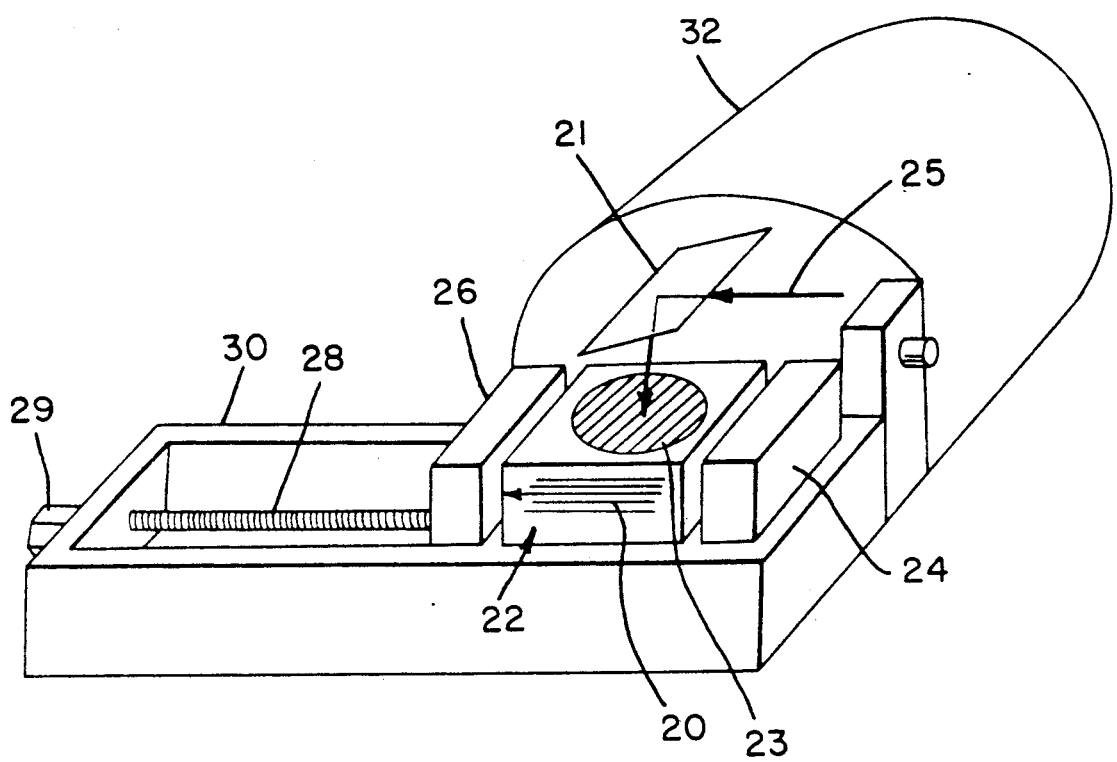
FIG. 2 depicts a construction of a preferred photoacoustic FT-IR cell used in the embodiment of FIG. 1.

FIG. 2 shows details of a preferred rheo-photoacoustic cell which includes the specimen holder. A specimen of thirty strands of PPTA fibers is prepared for disposition in a sealed chamber 22. IR radiation from source 10 (FIG. 1) is routed along path 25 by reflector 21 through a potassium bromide window 23 into the chamber 22. During IR irradiation, the chamber 22 is pressurize with an inert gas, such as helium, to an atmosphere level of about 1.1 atmospheres. A stationary clamping block 24 and moveable clamping block 26 provide means for holding and elongating the specimen 20. Rotation of a screw 28 engages its head 29 against housing 30 thereby to move the clamping block 26 to stress the specimen 20. At zero and various static load conditions, the specimen is irradiated with IR radiation as it resides in the pressurized chamber 22. A compartment 32 is also pressurized with inert gas in communication with the chamber 22. Pressurized inert gas in the chamber 22 and compartment 32 couples acoustic waves generated by the specimen with the detector head 15 (FIG. 1) which is also disposed in the compartment 32.

A method of determining relative bond association activity, or rheological measurements, is described in connection with FIGS. 3-5.

FIG. 3 depicts a cellular array and chemical bond structure of the structure of PPTA fibers. Of interest are the extensive intermolecular N—H O=C bond associations between neighboring chains. The vibrational modes of N—H and O=C stretching bands resonate at 3327 and 1657 $cm^{-1}$, respectively.

Figure 4:
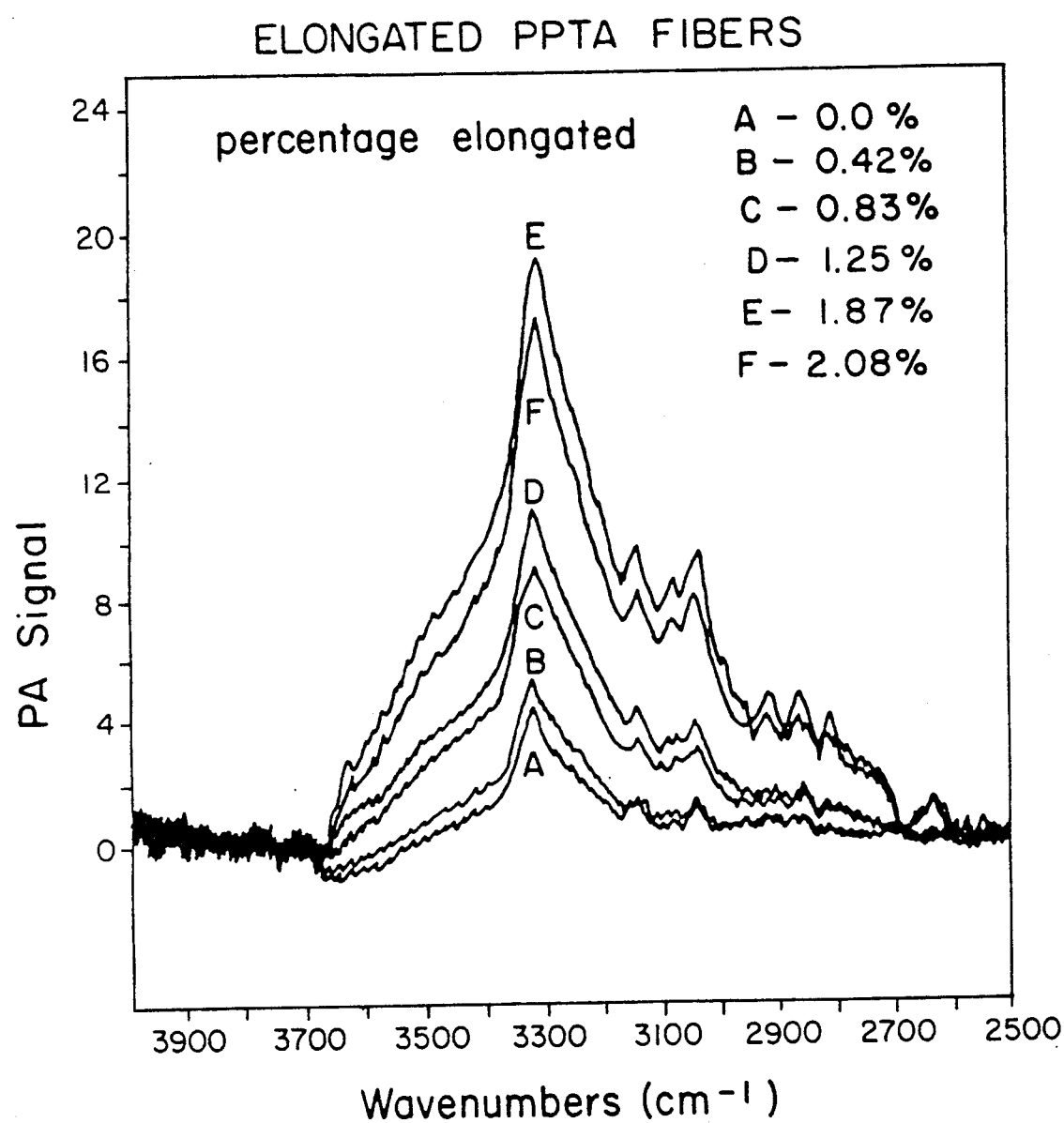
FIGS. 4–5 depict photoacoustic FT-IR signals generated by a specimen under various static load conditions A–F, and illustrate the nature of changes in different chemical bonds under load conditions.

FIG. 4 illustrates measured photoacoustic levels in the 4000-2500 $cm^{-1}$ band of PPTA fibers detected by the photoacoustic detector 14 (FIG. 1) and detector head 15 (FIG. 1) under successive static load conditions A-F. The spectral data of FIG. 4 was generated by processor 16 (FIG. 1). Static load conditions range from 0.0% to 2.08% elongation, as indicated in FIG. 4, which are achieved by displacing moveable clamping block 26 (FIG. 2) and irradiating the fibers at each load conditions. Spectral traces A-F, which each show peaks at 3327 $cm^{-1}$, represent stretching of the N—H bond in the specimen and correspond to the respective static load levels A-F. As noted by spectral trace E, the amplitude of the photoacoustic specturm reaches a peak at 1.67% elongation, and then falls off upon further elongation—indicating a weakening of the N—H bond. A photoacoustical spectral analysis of the O=C bond at 1656 $cm^{-1}$ shows the same behavior. A plot of percent elongation versus photoacoustic level was found to resemble the stress-strain relationship of these fibers obtained from an Instron mechanical analyzer, thus lending validity to the results.

Figure 5:
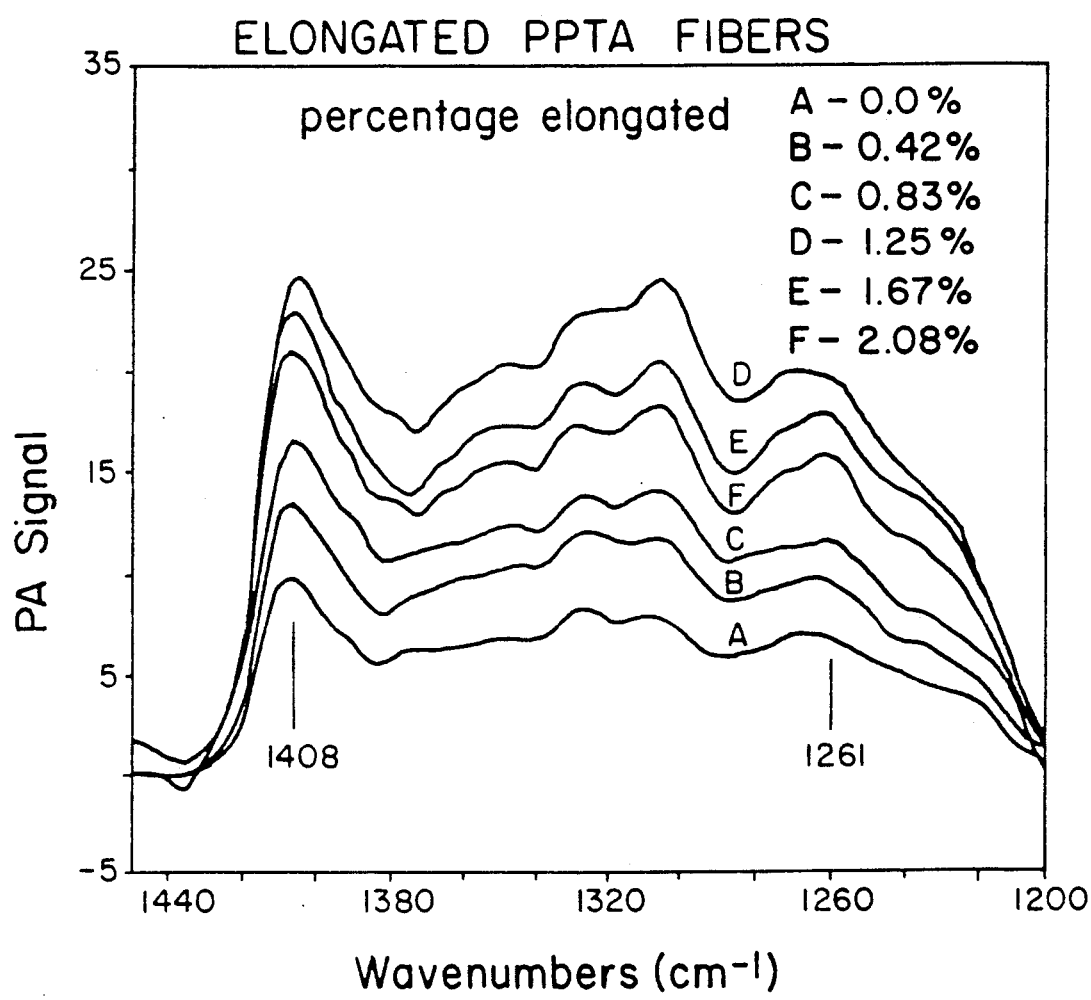

FIG. 5 depicts a rheo-photoacoustic FT-IR analysis of the C—C aromatic bending band at 1408 $cm^{-1}$ and the C—N in-plane bending band at 1261 cm$^{-1}$ of the PPTA polymer backbone. The same static elongation levels A-F were applied and corresponding spectral traces A-F were obtained. In this band, however, it is seen that a maximum photoacoustic spectrum is reached at 1.25% elongation (trace D) indicating a bond disassociation during the elongation process earlier than disassociation of the N—H C=O bond interaction. Accordingly, the invention enables measurement of relative weakening or bond disassociation on a molecular level.

A method of determining adhesive properties of composite materials by rheological measurements using photoacoustic IR techniques is described in connection with FIGS. 6A-6C, 7, and 8. This method finds particular use in thin-film and coatings technology.

Figure 6A:
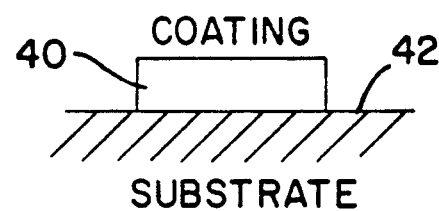
FIG. 6A—6C show successive stretching of a composite structure of siloxane coated polyethylene for illustrating interfacial failure analysis in accordance with method aspects of the present invention.
Figure 6B:
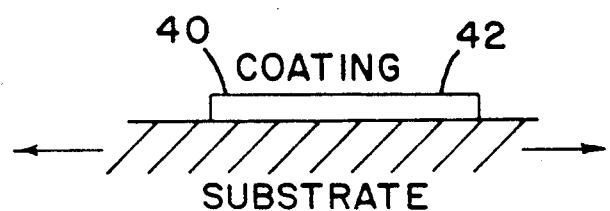
Figure 6C:
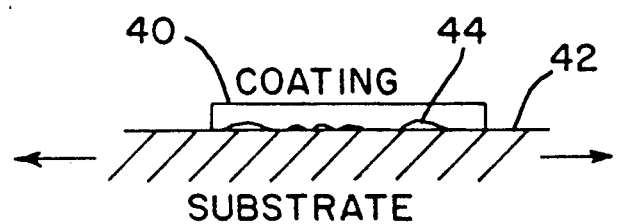

FIG. 6A-6C show a coating or film 40 of siloxane adhesively bound to a polyethylene substrate 42. The interfacial bond progressively weakens during increasing levels of stretching. FIG. 6A shows the composite structure under zero load condition. FIG. 6B depicts the structure under increased load, and FIG. 6C depicts microvoids at the substrate/coating boundary representing interfacial failure of the bond. A method of quantifying the failure point comprises generating a photoacoustic signal of the surface layer of coating 40 and detecting a change in the photoacoustic signal of the surface layer 40 brought about by photoacoustic effects of the substrate emanating through the microvoids 44.

Figure 7:
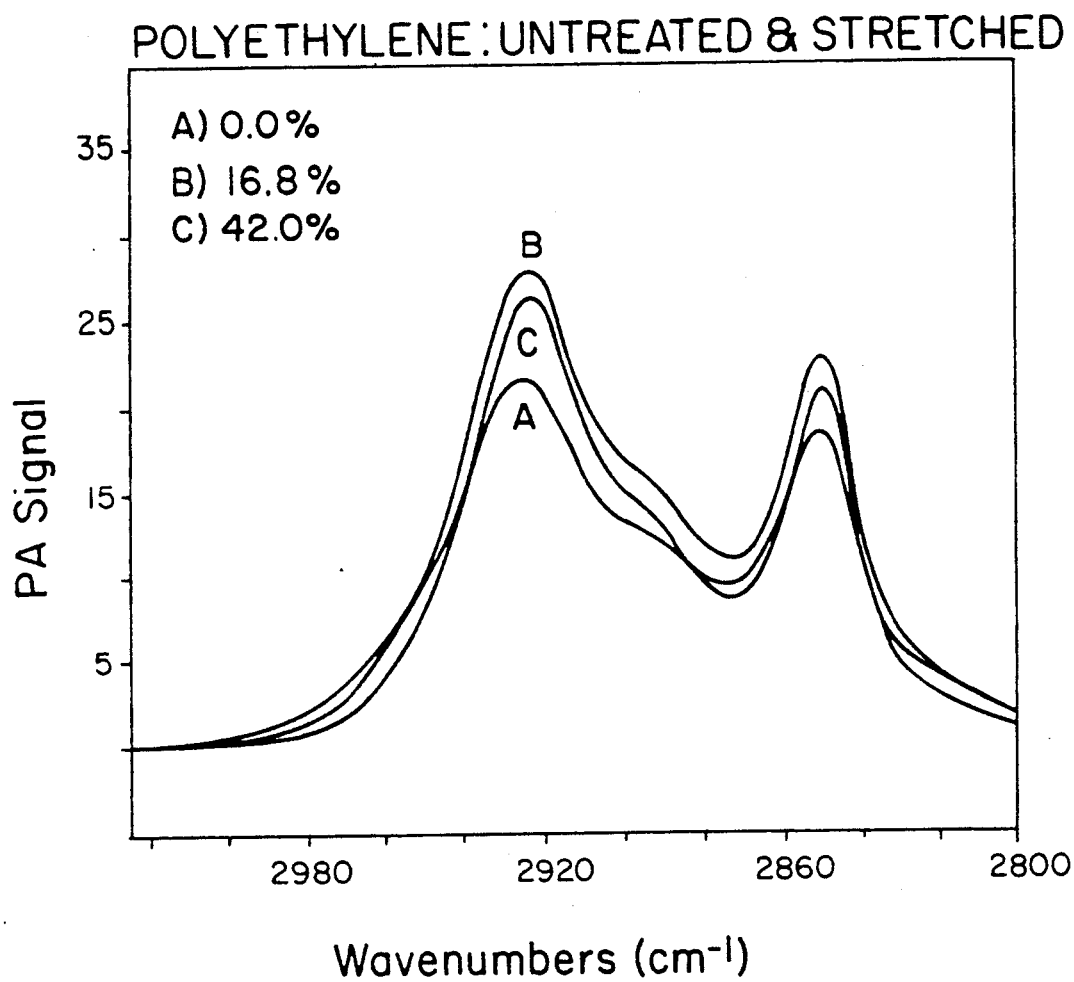
FIG. 7 shows frequency spectra of polyethylene under three different static load conditions useful for explaining interfacial failure analysis.
Figure 8:
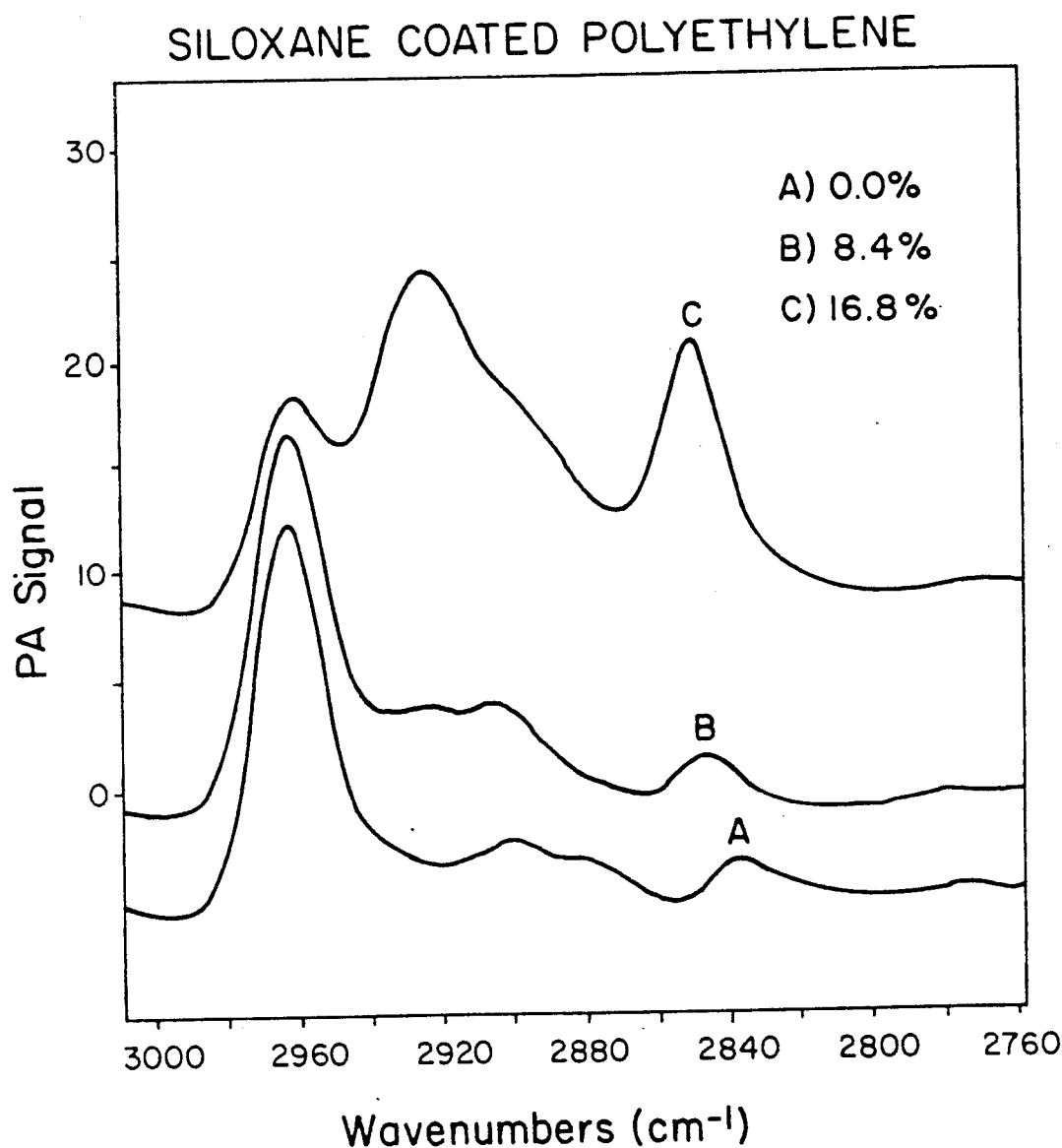
FIG. 8 shows frequency spectra of the composite siloxane/polyethylene structure under various static load conditions in connection with determining interfacial failures.

To illustrate further the method of detecting interfacial failure, FIG. 7 shows a rheo-photoacoustic FT-IR spectrum of polyethylene in the 3050-2800 cm$^{-1}$ wave number range at three levels of elongation A, B and C being 0.0%, 16.8% and 42%, respectively. It is seen that polyethylene attains its maximum elongation before the onset of failure at 16.8%. The bands at 2925 and 2850 cm$^{-1}$ are due to asymmetric and symmetric C-H stretching vibrations of the CH$_3$ groups in the polyethylene molecules. FIG. 8 shows the photoacoustic FT-IR spectra of the composite siloxane/polyethylene structure when elongated at 0.0% (trace A), 8.4% (trace B) and 16.8% (trace C). As clearly demonstrated, traces A and B predominately show only the characteristic siloxane photoacoustic FT-IR spectra. On the other hand, trace C, at 16.8% elongation, confirms an interfacial failure of the siloxane coating at some point below the polyethylene failure by virtue of appearance of the characteristic polyethylene bands at 2926 and 2850 cm$^{-1}$. Such failure may result in the formation of microvoids between the coating and substrate, allowing heat to escape which subsequently generates polyethylene characteristic acoustic waves through the siloxane.

The invention provides for rheo-photoacoustically analysis of materials of any shape, color or optical properties. Quantitative representations of material characteristics may be generated in any form which relate to differences in the photoacoustic spectrum under different static or dynamic conditions. Thus, the apparatus and methods described herein serve only illustrative and not restrictive purposes. It is accordingly the intent to embrace within the scope of the appended claim all such variations and modifications as may come to those skilled in the art in view of the teachings disclosed herein.

What is claimed to be secured by United States Letters Patent is:

1. An apparatus for indicating molecular characteristics of a specimen by rheo-photoacoustic means, said apparatus comprising:
   loading means for placing a load on said specimen,
   IR means for irradiating the speciment with infrared radiation,
   detecting means for detecting acoustic emissions of said specimen in response to said irradiation, and
   signal processing means for generating a representation of said molecular characteristics according to said acoustic emissions and the frequency of said infrared irradiation under at least two different load conditions.

2. An apparatus as recited in claim 1 wherein said signal processing means includes Fourier transform means for correlating levels of said acoustic emissions with the frequency spectrum of said IR means and display means for generating frequency-domain representations of said acoustic emissions in accordance with said IR means.

3. An apparatus as recited in claim 1 wherein said detecting means comprises a test chamber means for enclosing said specimen, specimen holding means for holding said specimen in a position to be irradiated by said IR means, and inert gas means for supplying said chamber means with inert gas for acoustically coupling said specimen and said detecting means.

4. An apparatus as recited in claim 3 wherein said test chamber means encloses said loading means for placing a predetermined load on said specimen thereby to obtain rheo-photoacoustic information of said specimen during examination.

5. An apparatus as recited in claim 4 wherein said predetermined load is includes one of stress, strain, and deformation.

6. An apparatus as recited in claim 5 wherein said predetermined load is dynamic.

7. A photoacoustic Fourier-transform infrared spectroscopic apparatus for generating a representation of molecular characteristics of a polymeric specimen by rheo-photoacoustic measurements, said apparatus comprising:
   IR means for irradiating the specimen with infrared radiation corresponding to vibrational frequencies of molecular bonds within said polymeric specimen,
   detecting means for detecting acoustic emissions of said specimen in response to infrared irradiation,
   specimen holding means for subjecting the specimen to a predetermined stress during said irradiation, and
   signal processing means for generating said representation of molecular characteristic of said specimen under said predetermined stress in a form related to said acoustic emissions and the frequency of said infrared irradiation.

8. An apparatus for examining molecular characteristics of a compound in accordance with vibrational modes of the molecules thereof, said apparatus comprising:
   excitation means for imparting energy upon said compound wherein said imparted energy is related to the frequency of said vibrational modes of the molecules of said compound,
   detecting means for detecting acoustic emissions of said compound in response to said imparted energy, and processing means for generating a representation of said molecular characteristics according to said acoustic emissions and said excitation means under different load conditions.

9. An apparatus as recited in claim 8 wherein said excitation means imparts energy having a frequency range related to the frequency range of said vibrational modes of the compound under examination, and wherein said processing means generates a frequency-domain magnitude of said acoustic emissions.

10. An apparatus as recited in claim 9 wherein said excitation means imparts infrared energy.

11. An apparatus as recited in claim 10 further including loading means for applying a load upon said compound during an examination thereof.

12. A method of performing rheological measurements of a material on a molecular level utilizing photoacoustic IR techniques comprising the steps of:
    irradiating the material with infrared radiation, and
    detecting acoustic signals generated by the material under differing load conditions applied to the material.

13. A method as recited in claim 12 further including the step of irradiating the material with infrared radiation having a frequency related to the stretching bands of molecular activity in the material.

14. A method as recited in claim 12 further including the step of generating a representation of the Fourier transform of the magnitude of the acoustic signal in the frequency domain.

15. A method as recited in claim 12 further comprising the step wherein the detecting step includes the step of acoustically coupling the material with said detecting and measuring by an inert gas.

16. A method as recited in claim 15 where said material is placed in a sealed environment including said inert gas, and said detecting is performed in said sealed environment.

17. A method of performing rheological measurements of a polymeric material on a molecular level utilizing photoacoustic IR techniques comprising the steps of:
    placing the material in an inert gas environment,
    irradiating the material with infrared radiation,
    detecting acoustic signals produced by the material under differing load conditions applied to the material, and
    generating representations of the detected acoustic signals in the frequency domain under differing load conditions of the material.

18. A method of detecting relative changes in molecular behavior of a molecular compound comprising the step of measuring photoacoustic infrared response under differing load conditions.

19. A method of analysis of materials on a molecular level comprising the step of performing rheo-photoacoustic Fourier-transform infrared spectroscopy.

20. A method of material analysis comprising the step of performing rheo-photoacoustic infrared spectroscopy.

21. A method of detecting an interfacial faiure of a composite structure of at least two materials comprising the step of detecting a change in photoacoustic FT-IR spectrum upon loading of the composite structure.

22. A method as recited in claim 21 further comprising the step of detecting an amplitude change in a band in the FT-IR frequency spectrum characteristic to at least one of said materials.

23. A method of detecting an interfacial failure of a composite polymeric structure of at least first and second materials comprising the step of comparing the photoacoustic FT-IR spectrum of at least one of said materials with the photoacoustic FT-IR spectrum of the composite structure under different loading conditions.

24. A method as recited in claim 23 further comprising the step of detecting an amplitude change in a band in the FT-IR frequency spectrum characteristic to at least one of said materials.

25. An apparatus as recited in claim 5 wherein said predetermined load is dynamic.

* * * * *